US012727765B2

(12) United States Patent
Geissler et al.

(10) Patent No.: US 12,727,765 B2
(45) Date of Patent: Sep. 8, 2026

(54) VETERINARY THERMOMETER AND METHOD OF MANAGING ANIMAL HEALTH CONSIDERING AMBIENT TEMPERATURE AND HUMIDITY CONDITIONS

(71) Applicant: Geissler Companies, LLC, Minneapolis, MN (US)

(72) Inventors: Randolph K. Geissler, Hudson, WI (US); Steve A. Lewis, Bloomington, MN (US); Greg Quakenbush, Valencia, CA (US); Gregory H. Smith, Prior Lake, MN (US)

(73) Assignee: Geissler Companies, LLC, Minneapolis, MN (US)

( * ) Notice: Subject to any disclaimer, the term of this patent is extended or adjusted under 35 U.S.C. 154(b) by 459 days.

(21) Appl. No.: 16/975,749

(22) PCT Filed: Aug. 21, 2020

(86) PCT No.: PCT/US2020/047444
§ 371 (c)(1),
(2) Date: Aug. 26, 2020

(87) PCT Pub. No.: WO2021/035154
PCT Pub. Date: Feb. 25, 2021

(65) Prior Publication Data

US 2022/0287568 A1 Sep. 15, 2022

Related U.S. Application Data

(60) Provisional application No. 62/889,918, filed on Aug. 21, 2019.

(51) Int. Cl.
*A61B 5/01* (2006.01)
*A61B 5/00* (2006.01)
(Continued)

(52) U.S. Cl.
CPC .............. *A61B 5/01* (2013.01); *A61B 5/0008* (2013.01); *A61B 5/742* (2013.01); *A61D 13/00* (2013.01);
(Continued)

(58) Field of Classification Search
CPC ....... A61B 5/01; A61B 5/0008; A61B 5/6873; A61B 2560/0252; A61B 2560/0431;
(Continued)

(56) References Cited

U.S. PATENT DOCUMENTS 3,151,739 A * 10/1964 Guffy .................... G01K 13/25 206/306
4,183,248 A * 1/1980 West ...................... G01K 13/20 374/134
(Continued)

FOREIGN PATENT DOCUMENTS

AU 2007271732 A1 * 2/2009 ............. A61D 13/00
CA 2609736 A1 * 5/2008 ............... G01K 1/14
(Continued)

OTHER PUBLICATIONS

16975749_2024-03-14_AU_2007271732_A1_H.pdf,Feb. 26, 2009.*
(Continued)

*Primary Examiner* — Mirellys Jagan
(74) *Attorney, Agent, or Firm* — Berg Hill Greenleaf Ruscitti LLP

(57) ABSTRACT

The invention includes a wireless multifunction veterinary thermometer device that communicates with a mobile communication device running an app for recording animal temperature data and to display animal treatment options considering the recorded data and ambient weather conditions. Treatment options may be determined by logic programmed within the app or by another computer program associated with a remote server and database. Data transfer
(Continued)

takes place between the mobile device and the remote server/database. A heat stress indicator is displayed for the user. If the indicator represents a high heat stress level, the app logic or remote computer program may automatically generate a recommended treatment option, or the user may determine an appropriate treatment.

10 Claims, 8 Drawing Sheets

(51) Int. Cl.
*A61D 13/00* (2006.01)
*G01K 13/20* (2021.01)
*G16H 40/67* (2018.01)

(52) U.S. Cl.
CPC ............. *G01K 13/20* (2021.01); *G16H 40/67* (2018.01); *A61B 2503/40* (2013.01); *A61B 2560/0252* (2013.01); *A61B 2560/0431* (2013.01); *A61B 2562/0271* (2013.01); *A61B 2562/029* (2013.01)

(58) Field of Classification Search
CPC .... A61B 2560/0475; A61B 2562/0271; G16H 40/67; G16H 10/60; G16H 50/20; G01K 13/20; A01K 11/006; A01B 5/0008; A61D 13/00
USPC .................................................. 374/142, 208
See application file for complete search history.

(56) References Cited

U.S. PATENT DOCUMENTS 4,236,236 A * 11/1980 Jaunin .................... G04G 21/02 368/200
5,018,875 A * 5/1991 Cook ....................... G01K 7/16 374/E7.018
6,000,845 A * 12/1999 Tymkewicz ........... G01K 1/146 374/163
6,046,674 A * 4/2000 Irwin ..................... G01K 1/024 374/E1.004
6,342,839 B1 * 1/2002 Curkendall .......... A01K 29/005 340/573.3
7,306,366 B1 * 12/2007 Camenzind ........ G01G 23/3728 374/170
7,448,799 B2 * 11/2008 Juhng .................... G01K 13/20 374/E13.002
8,235,591 B2 * 8/2012 Harris .................... G01K 13/00 374/150
10,620,055 B2 * 4/2020 Keller .................... G01K 13/00
10,809,135 B2 * 10/2020 Choi ................. H01M 10/4285
11,596,358 B2 * 3/2023 Abreu .................. A61B 5/6898
11,796,398 B2 * 10/2023 Hirschhorn ............ G01K 13/20
12,178,537 B2 * 12/2024 Mantri ................... B25J 9/1664
2002/0009119 A1 * 1/2002 Matthew ............ G01N 33/0009 374/45
2004/0264546 A1 * 12/2004 Wong ..................... G01K 13/20 374/E13.002
2005/0245839 A1 11/2005 Stivoric et al.
2006/0109886 A1 * 5/2006 Harris ................... G01J 5/0265 374/141
2007/0093880 A1 * 4/2007 Reever ................. A61B 5/6852 607/100
2008/0058670 A1 * 3/2008 Mainini ............... A61B 5/0002 600/549
2008/0175301 A1 * 7/2008 Chen ........................ G01K 1/14 374/121
2008/0259993 A1 * 10/2008 Blakeley ............... G01J 5/0846 374/E1.001
2010/0282184 A1 11/2010 Larson
2012/0068848 A1 * 3/2012 Campbell ............ A01K 29/005 340/573.1
2013/0245457 A1 * 9/2013 Kinsley ................ A61B 5/6886 600/549
2014/0003462 A1 * 1/2014 Roth ...................... G01K 13/20 374/E1.001
2015/0185088 A1 * 7/2015 Rabieirad .......... A61B 5/02055 374/122
2016/0109300 A1 * 4/2016 Lin .......................... G01K 1/08 374/100
2017/0254706 A1 * 9/2017 Ganrude .................. G01K 1/08

FOREIGN PATENT DOCUMENTS

CA 2472134 C * 8/2009 ............. G01K 1/083
CN 201639623 U * 11/2010
CN 207323452 U * 5/2018
CN 209027691 U * 6/2019
DE 202021102629 U1 * 11/2021 ............... G01K 1/08
WO WO-0101093 A1 * 1/2001 ........... G01K 13/002
WO WO-2018205030 A1 * 11/2018 ........... A61B 5/0008
WO WO-2019052607 A2 * 3/2019 ........... A01K 11/006
WO 2020094825 A1 5/2020

OTHER PUBLICATIONS

16975749_2024-03-14_CA_2472134_C_H.pdf,Aug. 18, 2009.*
16975749_2024-03-14_CN_207323452_U_H.pdf,May 8, 2018.*
16975749_2024-03-14_WO_0101093_A1_H.pdf,Jan. 4, 2001.*
16975749_2024-07-08_WO_2018205030_A1_H.pdf,Nov. 15, 2018.*
16975749_2025-01-31_CA_2609736_A1_H.pdf,May 15, 2008.*
International Search Report and Written Opinion in International Application No. PCT/US2020/047444 mailed on Feb. 22, 2021, 39 pages.
International Preliminary Report on Patentability in International Application No. PCT/US2020/047444 issued on Feb. 17, 2022, 7 pages.
Theurer, M. E., et al., "Effect of Mannheimia haemolytica pneumonia on behavior and physiologic responses of calves during high ambient environmental temperatures", Journal of Animal Science, May 8, 2013, pp. 3917-3929.
Theurer, Miles E., et al., "Effect of transportation during periods of high ambient temperature on physiologic and behavioral indices of beef heifers", Mar. 2013, pp. 481-490.
Theurer, Miles E., et al., "Relationship between rectal temperature at first treatment for bovine respiratory disease complex in feedlot calves and the probability of not finishing the production cycle", Dec. 1, 2014, pp. 1279-1285.
Theurer, Miles E., et al., "Effects of weather variables onthermoregulation of calves during periods of extreme heat", Mar. 2014, pp. 296-300.
Canadian Office Action on CA Application No. 3,149,006 issued on Feb. 26, 2024, 4 pages.

* cited by examiner

VETERINARY THERMOMETER AND METHOD OF MANAGING ANIMAL HEALTH CONSIDERING AMBIENT TEMPERATURE AND HUMIDITY CONDITIONS

CROSS REFERENCE TO RELATED APPLICATIONS

This application is a Patent Cooperation Treaty (PCT) application claiming priority to U.S. Provisional Patent Application Ser. No. 62/889,918 filed on Aug. 21, 2019 entitled VETERINARY THERMOMETER AND METHOD OF MANAGING ANIMAL HEALTH CONSIDERING AMBIENT TEMPERATURE AND HUMIDITY CONDITIONS, this prior application being incorporated herein by reference in its entirety.

FIELD OF THE INVENTION

The invention relates to a wireless veterinary thermometer, and more particularly, to a multifunction veterinary thermometer including measurement of ambient temperature and humidity measurements. The invention further includes a system and method for managing animal health considering heat stress as a function of the measured ambient temperature and humidity conditions and considering animal body temperature.

BACKGROUND OF THE INVENTION

Livestock are subjected to environmental stress during their production cycle. Livestock frequently suffer from respiratory diseases, generally referred to as bovine respiratory disease (BRD). BRD is highly contagious. A relatively healthy group of animals can quickly become infected considering the close proximity of the animals during feeding operations in a feed yard. Environmental factors can also contribute to health problems such as BRD. One significant environmental factor that adversely affects livestock health is high heat and humidity.

Presently, an animal's body temperature is still the most important measured health parameter that dictates what type of treatment an animal may require. The measurement of a rectal temperature (RT) is still the most accepted method of obtaining an accurate body temperature. Particularly in treatment of animals in feedlots, the RT remains as the primary determinant of whether an animal will receive an antibiotic treatment. While treatment protocols may vary between veterinarians or feedlots locations, RT is consistently used as the primary health determinant despite the advances in measuring animal health by different diagnostic protocols.

Considering RT is the primary determinant in how to treat an animal, any inaccuracy in the recording or interpretation of the RT can automatically result in either over-treatment or under-treatment of an animal. Neither situation is desirable since both may involve improper treatment decisions which will typically have economic and/or biologic consequences. For example, over-treatment of an animal through unnecessary rounds of administered antibiotics is clearly an economic loss. An example of under-treatment is when an animal does not receive an adequate administration of an antibiotic. The animal remains sick and may die, or the animal may require extensive emergency treatment making the animal infeasible for harvesting due to cost and timing.

An animal may have an elevated body temperature due either to the body itself creating more heat or because the body cannot lose an adequate amount of heat. The first circumstance relates to an animal being hyperpyrexic, meaning the animal itself has an elevated temperature due to activation of the animal's immune system that attempts to fight a disease. In other words, the hyperpyrexic circumstance relates to the animal having a "fever". The other situation involves the animal not having the capability to adequately lose heat due to ambient weather conditions outside of the animal's body, that is, elevated ambient temperature and/or humidity. This latter condition is referred to as a hyperthermic condition.

While livestock breeders have been extremely successful in optimizing animals such as cattle for meat production, cattle are particularly prone to overheating by elevated ambient temperature and humidity conditions. Many cattle have relatively small lung capacities, poor abilities to perspire, and inadequate capabilities to transfer body heat through the animal's mouth and tongue by "panting". Additional factors that may impact core body temperature of livestock include exercise and rumination.

Given that increased body temperature of an animal may originate from more than one source and perhaps from both hyperpyrexic and hyperthermic conditions, a caregiver is required to determine which factor or combination of factors contributes most to the increased body temperature. While some circumstances may make it easier for caregivers to determine which one is the prominent contributing factor, traditional rectal thermometers do not have the ability to measure ambient temperature and humidity conditions. Accordingly, a caregiver is not provided adequate data to make a recommendation as to whether treatment is required if a hyperthermic condition is a material contributing factor. Further, even if the caregiver may suspect a hyperthermic condition exists, the caregiver may not be capable of diagnosing an optimal treatment because the contributing extent of the hyperthermic condition is unknown.

Accordingly, there is a need to provide a temperature sensing device that has enhanced capabilities to include measurement of ambient weather conditions so conclusions can be made about measured body temperature and whether and by what degree an elevated body temperature is affected by the ambient weather conditions.

SUMMARY OF THE INVENTION

The invention in one preferred embodiment includes a wireless veterinary thermometer device that communicates with a mobile communication device. The wireless thermometer device includes a temperature sensing probe especially adapted for recording a rectal temperature of an animal. The temperature data is recorded and stored on the thermometer device. The temperature data may be selectively communicated to the mobile communication device which in turn, may upload temperature data and other data regarding the animal to a remote server and database. In this regard, the transfer of data to a remote server and database can also be described as providing a "cloud" solution for recording and storing temperature data, and subsequently, to determine a desired treatment protocol that can be communicated to a user within a communications network.

The wireless capability of the thermometer device enables data to be organized and stored in the remote server and database and therefore can be made immediately available for evaluation and analysis by caregivers and others who are granted access to the data. Further, because data is transferred and stored in a cloud solution, there is no practical limit as to the amount of data that can be stored and processed.

In addition to the temperature sensing capability of the thermometer device, the device may also be considered a multipurpose temperature sensing and recording device because the thermometer device furthers includes an ambient temperature sensor and a humidity sensor, each incorporated within the thermometer device. Accordingly, at the time of examination in which a rectal temperature is obtained for the animal, the ambient temperature and humidity conditions are simultaneously recorded and transmitted to the cloud solution. The ambient temperature and humidity data is used to determine a level of heat stress that the animal is experiencing. According to the invention, the ambient temperature and humidity data may be processed to generate a temperature heat index (THI). The temperature heat index may be a numerical value or score that is calculated as a function of the recorded ambient temperature and humidity. The THI along with the measure body temperature may be used to generate a treatment option for the caregiver. Logical relationships are established between animal body temperature and recorded ambient weather conditions. These relationships are then matched with treatment options so that a caregiver can automatically receive a recommended treatment option as discussed in greater detail below.

The structure of the multifunction thermometer device includes a housing which holds processing circuitry to include circuitry for processing temperature data as sensed by one or more temperature sensors located at the end or tip of the temperature sensor probe. The housing also includes separate ambient temperature and humidity sensors used to record the ambient temperature and humidity where the probe is being used. According to one preferred embodiment, the temperature and humidity measurements are integrated within a single sensor module.

A Bluetooth radio is further provided within the housing that enables recorded temperature data and humidity data to be wirelessly transmitted to a mobile communication and processing device such as a smart phone, or to another type of communication and processing device such as a laptop computer, tablet computer, or personal computer (PC).

The communication and processing device includes a software program or application (app) that enables the user to review recorded temperature data and to view treatment recommendations that may be generated as a result of the recorded temperature data. The treatment recommendations may also be affected by a calculated THI score in which an algorithm may determine a particular treatment recommendation based upon recorded body temperature and the calculated THI. For example, the treatment recommendation could include a recommended antibiotic treatment regimen, a recommended sorting action to isolate the animal from other animals within a feed yard environment, and/or a recommended feeding treatment. The treatment recommendation can be displayed on the user's smart phone, or whatever communication and processing device that the user may have at the time.

According to another embodiment of the invention, it may be considered a system for determining treatment for an animal considering animal body temperature and ambient temperature and humidity conditions comprising the multifunction thermometer device and a mobile communication device such as the smart phone.

Considering the above described features of the invention, according to one specific embodiment of the invention, it may be considered a multifunction thermometer device comprising: a housing; a temperature probe rotatably connected to the housing and selectively placed between a stored position and an extended operable position; a body temperature sensor incorporated in said temperature probe especially adapted for measuring rectal temperature of an animal; a display module secured to said housing for displaying measured temperature and other selected measured parameters; an ambient temperature sensor within said housing; an ambient humidity sensor within said housing; a microprocessor within said housing and communicating with each of said sensors; a data storage element communicating with said microprocessor for storing information processed by said microprocessor including temperature data including the animal body temperature, the ambient temperature and present humidity conditions; and a wireless radio.

A number of optional features may be associated with the aforementioned specific embodiment. These features may include: (a) a heating coil disposed in said temperature probe and communicating with said body temperature sensor in order to selectively heat the device prior to use; (b) wherein said temperature probe further includes a sleeve and a probe extension extending distally from said sleeve; (c) wherein said temperature probe further includes a sleeve and a probe extension extending distally from said sleeve; and a heating coil is disposed in said temperature probe and in contact with said probe extension to thereby selectively heat said body temperature sensor prior to use; (d) wherein said probe extension is made of a heat conductive material including copper; (e) a rotatable base interconnecting a proximal end of said temperature probe to said housing enabling said temperature probe to be placed in a stored position or an extended position; (f) control buttons on said housing and communicating with said microprocessor enabling a user to selectively control functions of said device; and (g) an RFID reader disposed in said housing and communicating with said microprocessor, said RFID reader receiving identification data associated with the animal from a tag of the animal, said RFID reader providing said identification data to said microprocessor and stored in said data storage element wherein the identification data and temperature are linked for each animal whose temperature is taken.

According to another specific embodiment of the invention, it may be considered a system for determining treatment for an animal considering animal body temperature and ambient temperature and humidity conditions comprising: (a) a multifunction thermometer device comprising; a housing; a temperature probe rotatably connected to the housing and being selectively placed between a stored position and an extended operable position; a body temperature sensor incorporated in said temperature probe especially adapted for measuring rectal temperature of an animal; a display module secured to said housing for displaying measured temperature and other selected measured parameters; an ambient temperature sensor within said housing; an ambient humidity sensor within said housing; a microprocessor within said housing and communicating with each of said sensors; a data storage element communicating with said microprocessor for storing information processed by said microprocessor; and a first wireless radio; and (b) a mobile communication device comprising: a second wireless radio communicating with said first wireless radio to receive recorded temperature and humidity data of said thermometer device; a software application running on said communication device especially adapted for displaying user interfaces associated with said temperature and humidity data and for displaying a heat stress indicator.

A number of optional features may be associated with the aforementioned second specific embodiment. These features may include: (a) wherein said heat stress indicator includes a numerical heat stress indicator derived from a temperature heat index (THI); (b) wherein said user interfaces further include a visual display of a recommended treatment derived from a consideration of the recorded rectal temperature and the heat stress indicator (c) a heating coil disposed in said temperature probe and communicating with said body temperature sensor in order to selectively heat the device prior to use; and (d) an RFID reader disposed in said housing and communicating with said microprocessor, said RFID reader receiving identification data associated with the animal from an electronic tag of the animal, said RFID reader providing said identification data to said microprocessor and stored in said data storage element wherein the identification data and temperature are linked for each animal whose temperature is taken.

According to yet another specific embodiment of the invention, it may be considered a method for determining whether to treat an animal based upon measurement of body temperature and ambient weather conditions comprising: (a) providing a multifunction thermometer device comprising a housing; a temperature probe; a body temperature sensor incorporated in said temperature probe especially adapted for measuring rectal temperature of an animal; a display module secured to said housing for displaying measured temperature and other selected measured parameters; an ambient temperature and humidity sensor module within said housing; a microprocessor within said housing and communicating with each of said sensors; a data storage element communicating with said microprocessor for storing information processed by said microprocessor; and a first wireless radio; positioning said probe for taking a rectal temperature of the animal; (b) recording the rectal temperature and storing corresponding rectal temperature data in said data storage element; (c) recording the ambient temperature and humidity, and storing corresponding ambient temperature and humidity data in said data storage element; (d) automatically determining by said processor, a heat stress indication by a logical relationship established between the animal body temperature and the ambient temperature and humidity conditions; (e) storing said heat stress indication in said data storage element; (f) providing a wireless radio coupled to said thermometer device; (g) wirelessly transmitting selected rectal temperature data and ambient temperature and humidity data to a remote communication device; (h) providing a software application running on said remote communication device especially adapted for generating user interfaces containing information corresponding to said rectal temperature data and ambient temperature and humidity data; and (i) generating at least one user interface on said remote communication device including said information corresponding to said rectal temperature data and ambient temperature and humidity data.

A number of optional features may be associated with the aforementioned third specific embodiment. These features may include: (a) generating at least one user interface on said remote communication device including a representation of said heat stress indicator; (b) said heat stress indicator includes a number; (c) at least one of said user interfaces includes a recommended treatment option considering a combination of said rectal temperature and said heat stress indicator; (d) providing an RFID reader disposed in said housing and communicating with said microprocessor; and (e) said RFID reader receiving identification data associated with the animal from an electronic tag of the animal; and said RFID reader providing said identification data to said microprocessor and stored in said data storage element wherein the identification data and temperature are linked for each animal whose temperature is taken.

According to yet another specific embodiment of the invention, it may be considered a non-transitory computer-readable medium containing computer executable instructions, wherein, when executed by a computer processor, the instructions cause the computer processor to execute a method to determine a recommended treatment option for an animal comprising: (a) instructions to receive and store data corresponding to recorded animal body temperature; (b) instructions to receive and store data corresponding to recorded ambient temperature and humidity; (c) instructions to execute an algorithm to determine whether the animal should receive treatment, wherein the algorithm comprises input variables corresponding to the recorded body temperature and to the recorded ambient temperature and humidity; and (d) instructions to generate a user interface associated with the computer processor for displaying to a user a treatment option for the animal.

A number of optional features may be associated with the aforementioned fourth specific embodiment. These features may include: (a) wherein execution of said algorithm includes automatically generating a numerical heat stress indicator; and (b) instructions to receive and store identification data obtained from an RFID reader disposed in said housing and communicating with said microprocessor, said identification data being associated with the animal from an electronic tag of the animal; and instructions to link the identification data for the animal to corresponding temperature data of the animal.

Other features and advantages of the invention will become apparent by a review of the following detailed description taken in conjunction with the drawings.

DETAILED DESCRIPTION

Figure 1:
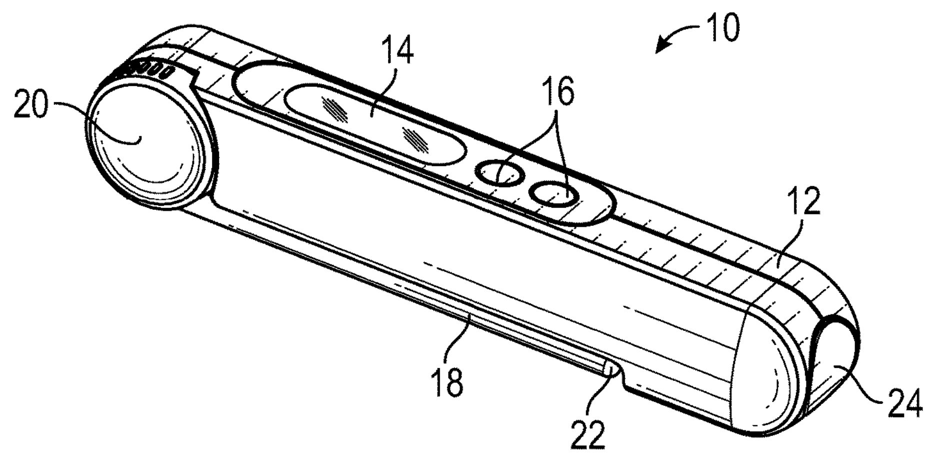
FIG. 1 is a perspective view of the multifunction thermometer device of the invention.
Figure 2:
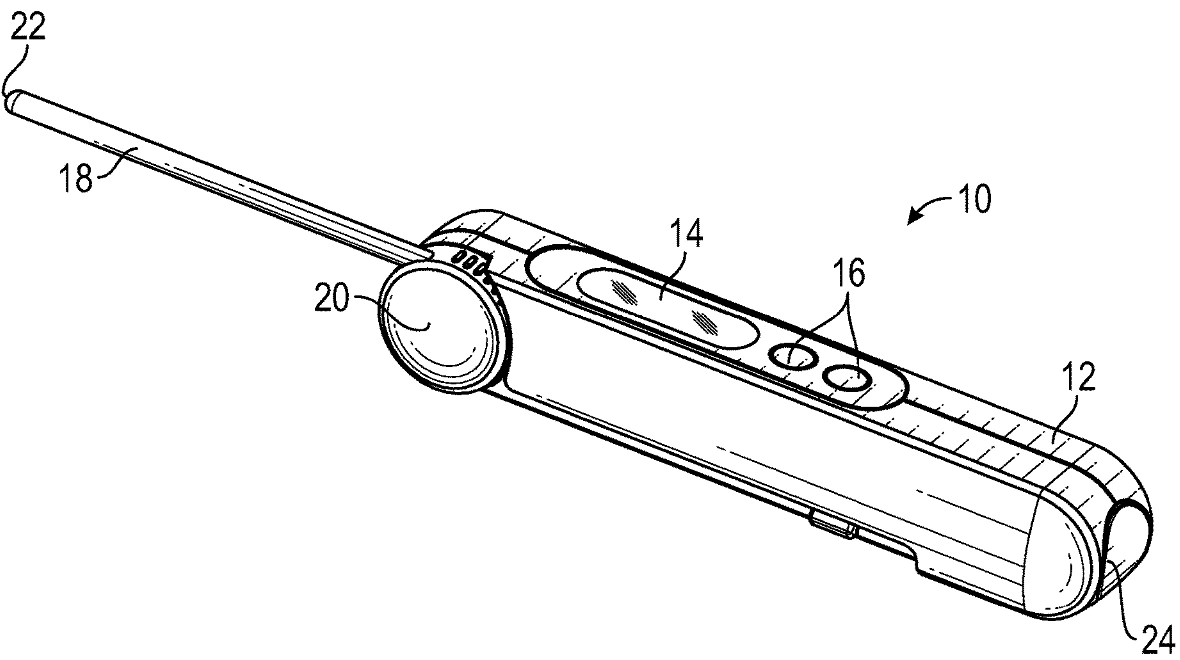
FIG. 2 is another perspective view of the multifunction thermometer device showing the temperature sensor probe in an extended position.

FIG. 1 illustrates a preferred embodiment of the multifunction thermometer device 10 of the invention. The device 10 has a housing 12 that holds the components of the device. An integral display module 14 provides a visual display to the user to include user selectable information such as the reading of measured body temperature of an animal, and the measured ambient temperature and humidity. Control buttons 16 are provided to control operation of the device, such as a power on/off button and a display control button that allows a user to select the format and content of the display 14. A temperature probe 18 is secured to the housing by a rotatable base 20 that enables the probe to be placed in a stored position as shown in FIG. 1 or a deployed or extended position shown in FIG. 2. The probe 18 has one or more temperature sensors located at or near the tip 22 of the probe 18. A removable cap 24 is provided to seal the opening of a threaded connection port 32 as discussed in greater detail below.

The device 10 is intended to be portable and pocket sized so a user may conveniently carry the device to any desired location. When the user decides to take a temperature measurement, the user powers on the device and extends the probe 18 to the deployed position. The device is then placed within the rectum of the animal to take a temperature measurement. The temperature measurement may be automatically recorded after a predetermined period of time, or the user may watch the display module 14 to track the measured temperature to confirm when a steady-state temperature measurement has been achieved. At that time, the user may depress one of the control buttons in order to capture and record the temperature at that time.

Figures 3, 4:
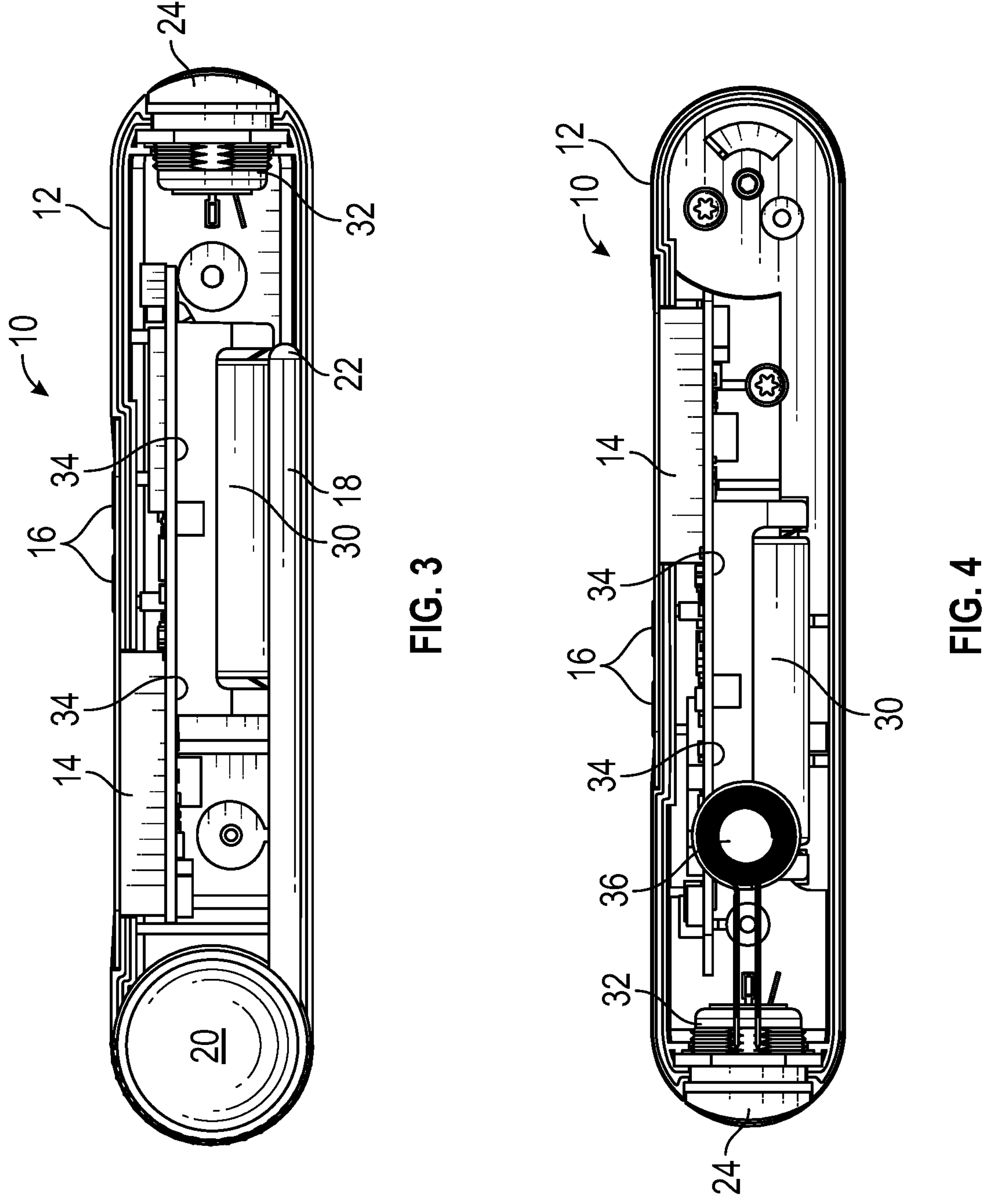
FIG. 3 is a first cross-sectional view showing interior details of the device.
FIG. 4 is a second cross-sectional view showing further interior details of the device.

FIGS. 3 and 4 illustrate some of the interior components of the device 10. One option for powering the device includes the use of a battery 30 located within the housing 12. The threaded connection port 32 is covered by the cap 24 as shown. The connection port 32 accommodates use of an external temperature sensor as discussed with respect to the embodiment of FIG. 5. A main circuit board 34 is disposed within the housing to support device circuitry to include the integral display module 14. Another option for powering the device includes an inductive charger 36.

Figure 5:
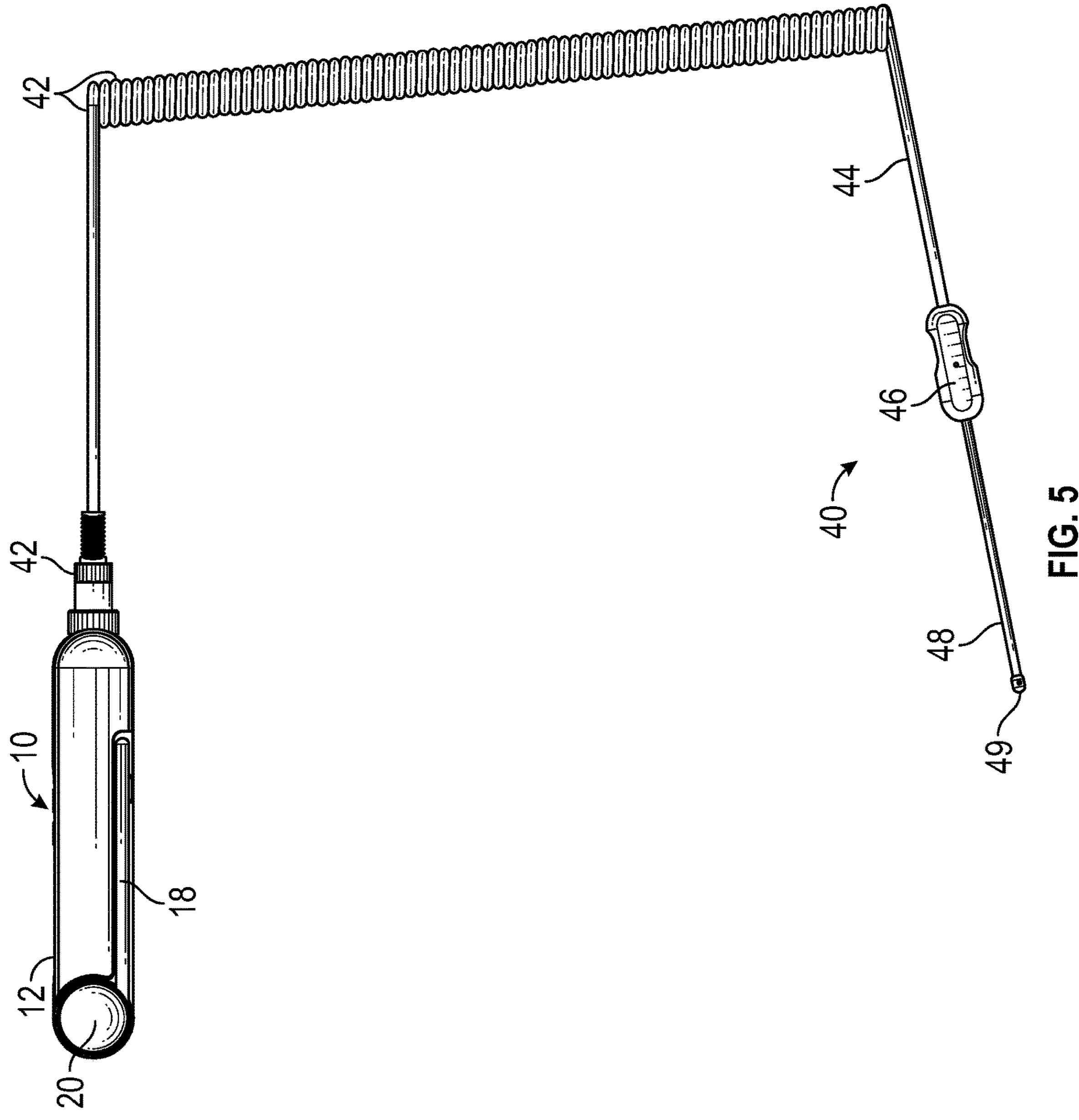
FIG. 5 is a perspective view of another embodiment of the temperature device showing an external temperature probe that may be used to expand a distance in which to obtain access to an animal.

Referring to FIG. 5, another embodiment of the multifunction temperature device is illustrated. This embodiment includes the use of an external temperature probe 40 connected to the device 10 by a retractable cord or cable 44. One end of the probe 40 includes a probe base 42 which is connected to the device 10 by the threaded connection port 32. The cord or cable 44 is flexible so the temperature probe 48 can be placed at a desired distance from the device 10. For example, when an animal is placed within a chute upon receiving the animal in a feed yard, for safety purposes, the user may desire to place the probe 48 and then retreat to a more safe position without having to hold the device 10 in close proximity to the animal. In this way, the device 10 can be used at a safe offset distance from the animal as it is being evaluated. The probe 48 may further include a bulbous shaped tip 49 which may prevent inadvertent perforation of the animal's bowel tissue upon insertion. As with the temperature probe 18, the probe 48 may have one or more temperature sensors. An adapter 46 is provided so that different types and lengths of probes 48 may be selected by the user.

Figure 6:
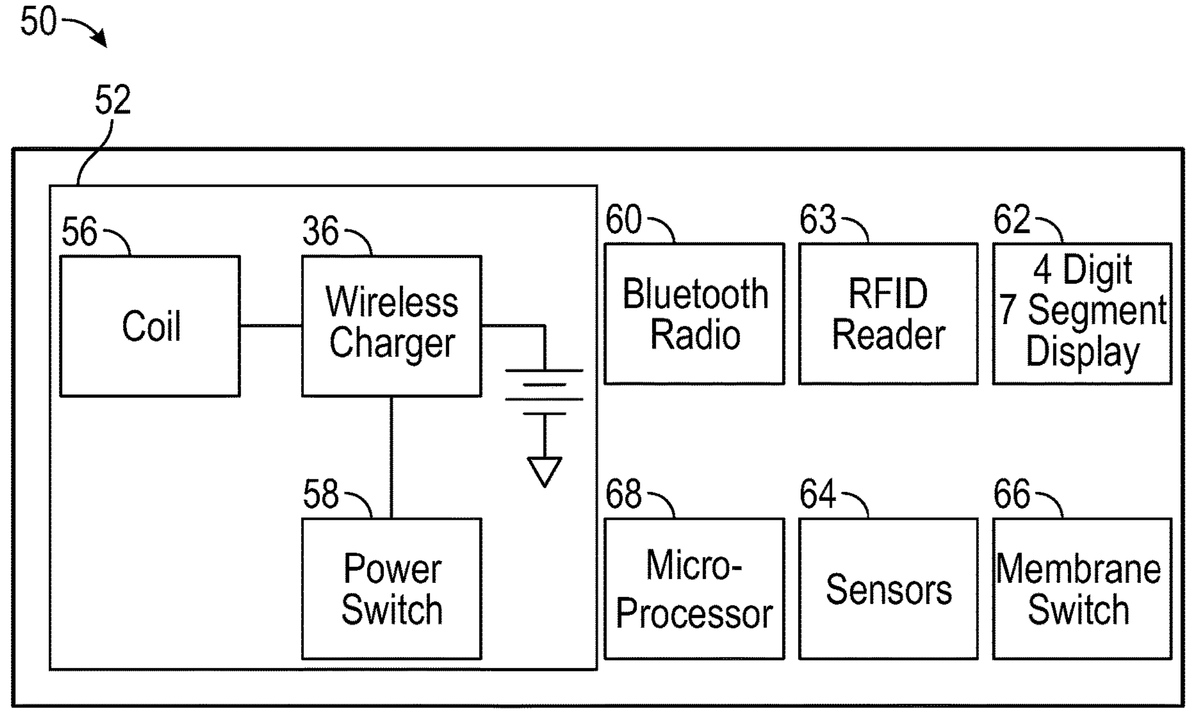
FIG. 6 is a simplified schematic block diagram showing functional components of the multifunction thermometer device.

FIG. 6 illustrates a simplified schematic diagram 50 showing some of the major functions of the circuits within the housing 12. A power module 52 is provided for powering the device to include an alternate power source in the form of the inductive charger 36. The inductive charger 36 communicates with a coil 56 that stores electrical energy transferred by magnetic induction. Wireless charging technology involves the use of magnetic induction to transfer power from a transmitter to a receiver. Accordingly, the device 10 acts as a receiver to receive power transferred from a transmitter (not shown) such as a charging station to which the device may be coupled for charging. A power switch 58 enables power to be switched between the coil 56 and the battery 30.

A Bluetooth radio 60 is provided for wirelessly transmitting and receiving signals from a communication device, such as a mobile communication device. Accordingly, a local database (not shown) associated with the microprocessor 68 may temporarily store recorded temperature data, humidity data, and other information so that it may be subsequently transmitted to the mobile communication device. The integral display module 14 may incorporate a four-digit, seven segment display 62, which is a convenient manner to display recorded temperatures and other data. The sensors 64 of the invention include temperature sensors incorporated on the temperature probes 18 and 48. The sensors may include thermistors, thermocouples, RTDs, or other known temperature sensing elements. These sensors 64 further include an ambient temperature sensor (not shown) that is mounted within the housing and captures ambient temperature conditions. Yet another sensor includes a humidity sensor (not shown) that is also incorporated within the housing 12 and captures ambient humidity conditions. One example of a combined temperature and humidity sensor that may be used for obtaining ambient temperature and humidity conditions is a sensor manufactured by ST Microelectronics, manufacturer part number HTS221. This example sensor has a sensing element comprising a polymer dielectric planar capacitor and a mixed signal ASIC to provide measured data through digital serial interfaces. FIG. 5 also shows membrane switches 66 that may be used to control device functionality to include setting the user display according to a user's preference.

The multifunction temperature device also has an optional RFID capability that enables the device to remotely communicate with an electronic RFID tag secured to an animal. As shown, the circuitry of the device may therefore include an RFID reader 63 that communicates with the RFID tag of the animal whose temperature is being taken. The RFID reader 63 can be either a passive reader or an active reader depending upon the type of tag that may be encountered. A passive RFID reader is one that only receives radio signals from active tags, i.e., those tags that are self-powered and transmit only. An active RFID reader is one that transmits an interrogator signal and receives authentication replies from passive tags. Alternatively, an active RFID reader can be one that communicates with active tags that are energized or "awoken" by an interrogator signal from the active RFID reader that subsequently receives reply signals from the active tag.

Once a RFID tag has been successfully interrogated by the RFID reader 63, the identification data of the particular animal associated with the RFID tag may be directly recorded on the local database of the microprocessor 68 and linked to the corresponding temperature data for the particular animal. Accordingly, a data bus (not shown) may interconnect the RFID reader 63 for transfer of data to the microprocessor 68. By use of the RFID reader, identification of the animal is made easier and eliminates manual entry of data by a user of the device.

Figure 7:
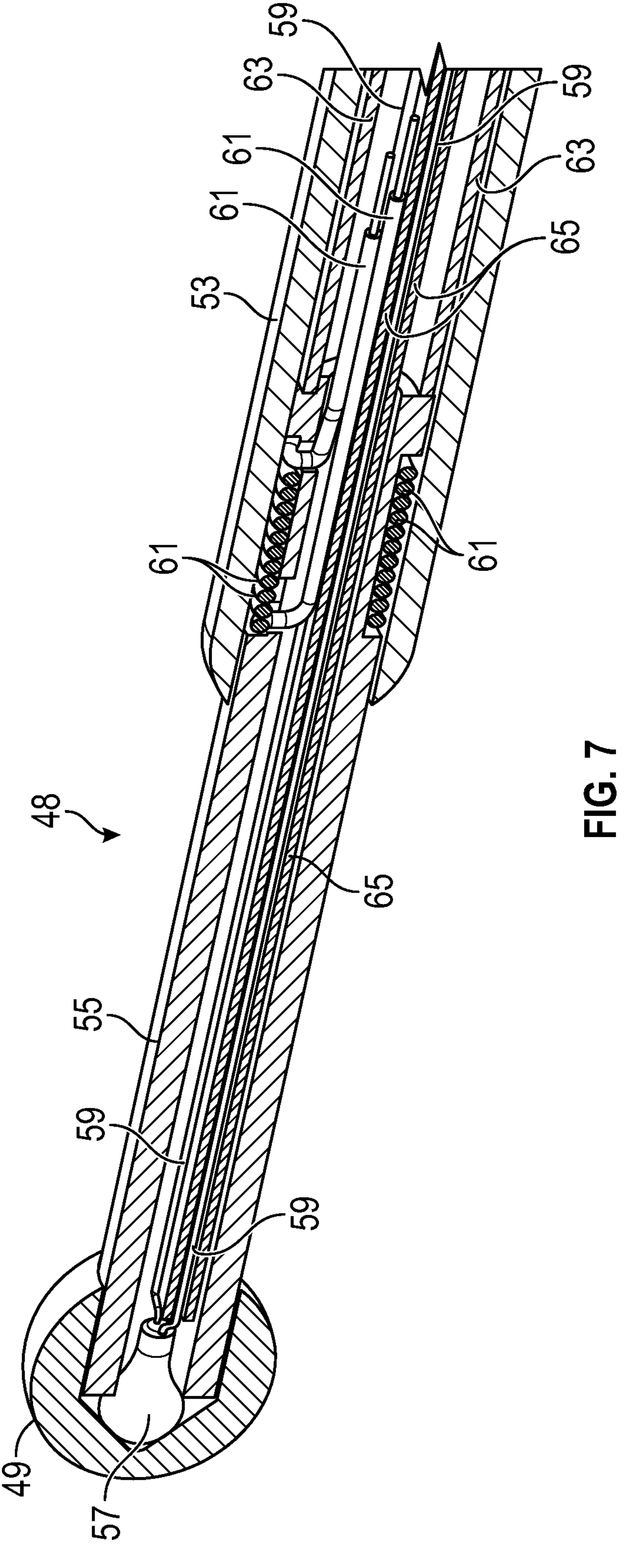
FIG. 7 is an enlarged cross-sectional view of the distal end of the temperature sensor probe illustrating construction details according to an embodiment of the invention.

FIG. 7 is an enlarged cross-sectional view of the distal end of the temperature sensor probe illustrating construction details according to an embodiment of the invention. The body of the probe 48 is illustrated in this embodiment as comprising a probe extension 55 and an outer sleeve 53 that is secured to a proximal end of the probe extension 55. The distal tip 49 is a rounded and enlarged to prevent damaging the tissue of an animal by puncturing. The rounded distal tip also helps to prevent the tip from becoming inadvertently lodged within the animal which could occur with a more pointed tip. Interior details of the probe body 48 further illustrate a temperature sensor in the form of a resistance temperature detector (RTD) 57. An RTD is a temperature sensor that contains a resistive element that changes electrical resistance as its temperature changes. A common construction for an RTD includes a length of conductive filament wrapped around a nonconductive core such as glass or ceramic. A protective sheath surrounds the coiled filament. Conductive wires connect to the conductive filament and which provide electric current through the filament and to measure changes in resistance. In connection with this type of construction, what is more specifically illustrated in FIG. 7 is the protective sheath or cover of the RTD 57 with two conductive wires 59 that connect to the RTD and extend through the probe. The free ends of the wires 59 (not shown) are connected to a resistance measuring element (not shown) that may be incorporated on circuitry of the device that communicates with the microprocessor 68 for transfer of temperature data and subsequent storage of temperature data on a local database associated with the microprocessor.

Another feature of the device includes a heating element that comprises a heating coil made from resistive wire that selectively heats the probe extension 55. As shown, the heating coil is located and secured to a proximal end of the probe extension 55 within the sleeve 53. The heating coil is formed by wraps of resistive wire 61 around a selected length of the proximal end of the probe extension 55 within the sleeve 53. The free ends of the wire 61 (not shown) extend back through the body of the probe and connect to an electrical source (not shown). Electrical current is selectively applied to the wire 61 in order to heat the probe extension 55 which in turn, heats the RTD 57 considering its proximity to the distal end of the probe extension 55. The probe extension 55 can be made of a highly conductive material such as copper to accommodate conductive heat transfer from the heating coil.

Other features illustrated in FIG. 7 include one or more interior sleeves 63 and 65 that provide interior protected passageways for the RTD wires 59 and resistive wire 61. These sleeves can also add desired stiffness and strength to the probe.

According to one aspect of the preferred embodiment, the heating coil may terminate approximately 1 inch from the end of the probe. With this distance, there is enough spacing between the RTD 57 and the heating coil to create a temperature gradient when the probe is inserted in the animal. Upon insertion, the temperature at the tip of the probe will ramp up quickly to the animal's temperature. The probe is maintained in a heated condition slightly below the expected potential temperature range of the animal. The heating coil is deenergized once the temperature reaches 96° F., so the heating coil does not contribute to the probe temperature once the probe is inserted into the animal.

It is a great advantage, particularly in cold weather conditions, to maintain the probe at a heated condition so that the temperature of the animal can be quickly obtained without having to wait for the probe to heat up. A probe during use in winter months may have to overcome a 70 or 80° F. temperature differential when comparing ambient temperatures to the temperature of the animal. With the preheated probe of the invention, the temperature differential is drastically reduced therefore enabling the temperature to be taken quickly and efficiently.

In connection with this advantage, the heating coil preferably keeps the probe at a heated temperature when the probe is not being used during a temperature reading. The device can be programmed such that when the probe is in use, the heating coil is shut off to ensure the heating coil does not maintain the temperature of the probe above a normal temperature of the animal being evaluated. For example, for use with cattle, the heating coil can be set to maintain the probe at around 96° F. The average temperature of an adult cow is around 101.5° F., thus a differential is provided between the heated probe temperature and the animal temperature. By "preheating" the coil, the delay in heating the RTD can be minimized thereby reducing the amount of time required to take the temperature of the animal. Hundreds of animals may need to be processed in a short period of time; therefore, the device must be able quickly and accurately determine temperatures without significant delay between animals being processed.

Figure 8:
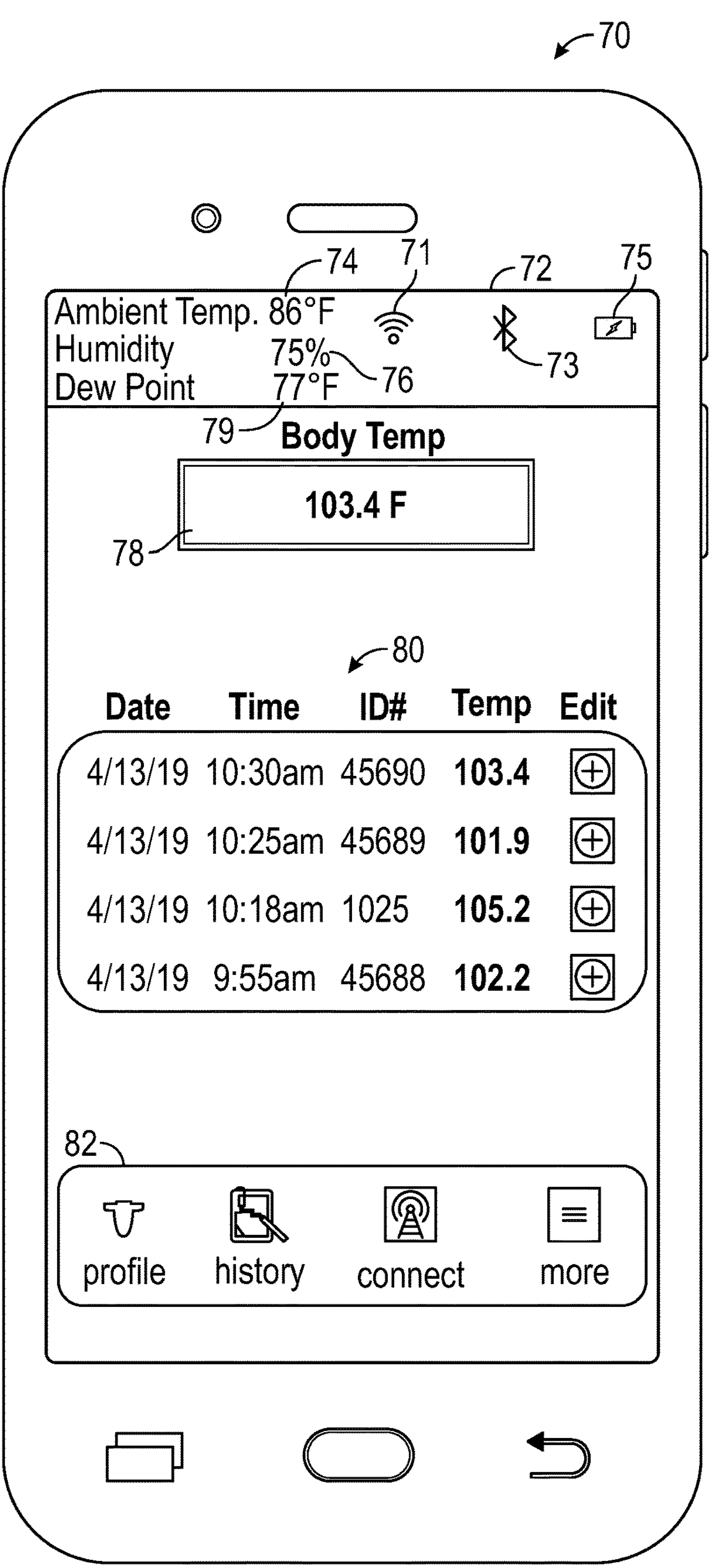
FIG. 8 is an example user interface that shows functionality associated with a user app that may be viewed by a user carrying a smart phone or other mobile communication device.

FIG. 8 illustrates a mobile communication device 70 such as a wireless/cellular telephone or smart phone that runs a mobile application on the device 70. A mobile application (app) is a computer program or software application designed to run on a mobile device such as a cellular phone or tablet. Accordingly, the term "app" is intended to mean the broad spectrum of software applications that are capable of being run on a mobile device, without limitation as to a particular platform. Accordingly, an app of the invention could include a native app, a hybrid app, a web-based app, or a combination thereof.

The user interface of the app 72 may display a wide variety of information to include the measured ambient temperature 74, the measured ambient humidity 76, the dew point 79 and the recorded body temperature 78 of the animal. Preferably, the body temperature of the animal is the rectal temperature; however, in some cases, it may be desired to supplement the body temperature with other temperature sensing devices that could be displayed on the app. Therefore, it should be understood that the user display shown on app 72 is not limited to only a body temperature obtained by a rectal thermometer. The user interface of the app 72 may also display other features such as the status of a wireless connection 71, a status of a Bluetooth connection 73, and a battery status 75.

The user display 72 of the app further provides a data field 80 with information regarding time/date stamps when measurements were recorded, as well as identification of the particular animal for which measurements were recorded. Each animal received into a location such as a feed yard is identified by a unique tag number. The data field 80 therefore shows an ID number associated with the animal. The user has an edit option which may enable a user to modify the recorded information, to add information, or to otherwise manipulate the information shown in the data field. Yet another field shown within the user interface of the app 72 is a toolbar 82 that enables the user to access other functions of the app. For example, the toolbar 82 shows four selectable options or button, namely, "profile", "history", "connect", and "more" options. The "profile" option may enable the user to view another user interface showing the particular profile of an animal which could include other recorded data about the animal to include its origin, weight, etc. The "history" option may enable the user to view another user interface showing historical data about the animal, such as any medical history and any prior treatments received. The "connect" option may enable the user to view another user interface showing other wireless connection options, such as another Bluetooth network enabling the user to connect to one or multiple other thermometer devices. The "more" option may enable the user to user configurable user screens or functions relating to operation of the connected thermometer devices.

Figure 9:
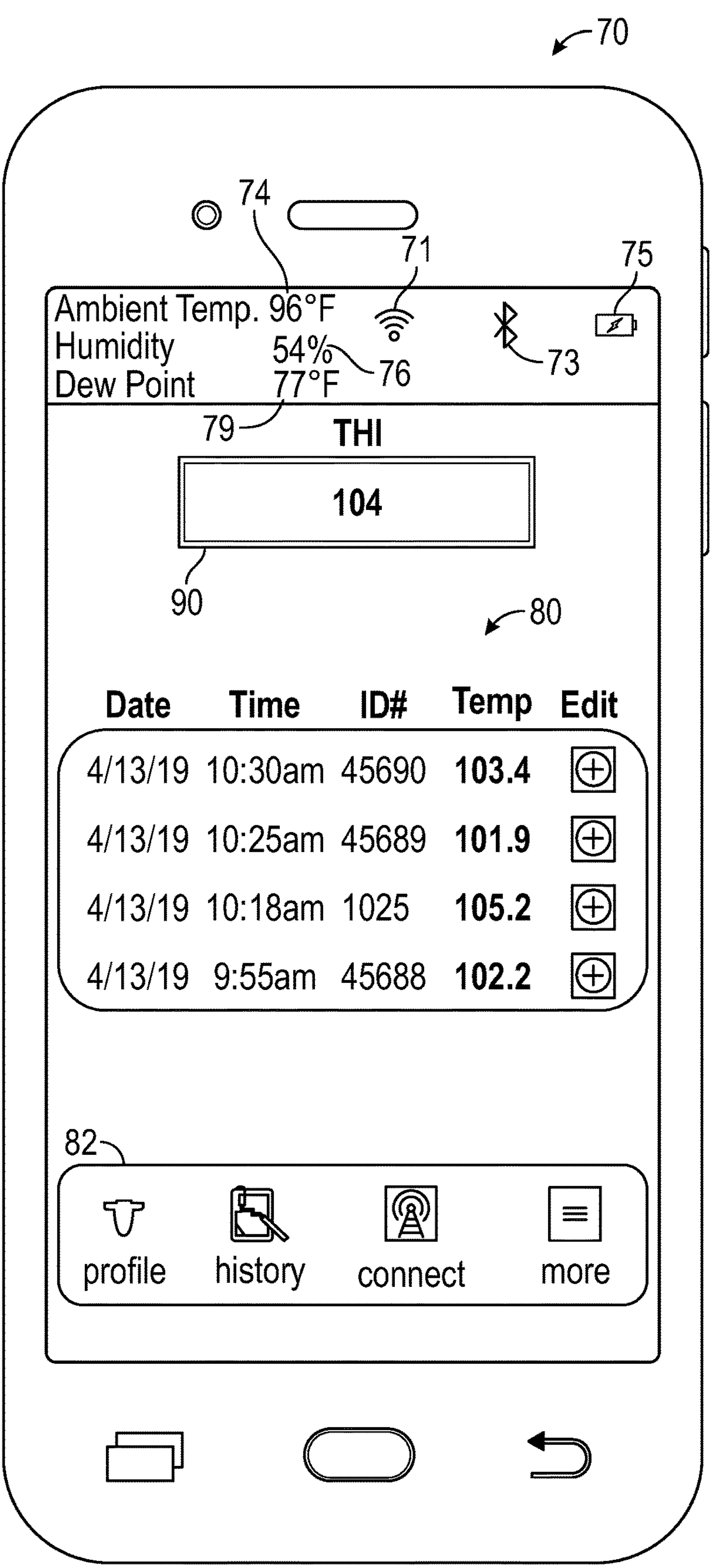
FIG. 9 is another example user interface that shows further functionality associated with the user app.

Referring to FIG. 9, the user interface 72 for the app illustrates alternate information in the temperature field 90, namely, a calculated temperature heat index (THI). As discussed, the temperature heat index is a measure of the degree to which ambient temperature and humidity places stress on an animal. Accordingly, the THI may automatically trigger a recommended treatment for the animal, also considering the measured body temperature. Therefore, according to another aspect of the invention, it is contemplated that the app may further display a recommended treatment (not shown) as may be accessed by the user in another user display. The recommended treatment could include, for example, administration of an antibiotic, transfer of the animal to a hospital pen within a feed yard, or any another remedial action to be undertaken to stabilize/improve the animal's physical condition.

Figure 10:
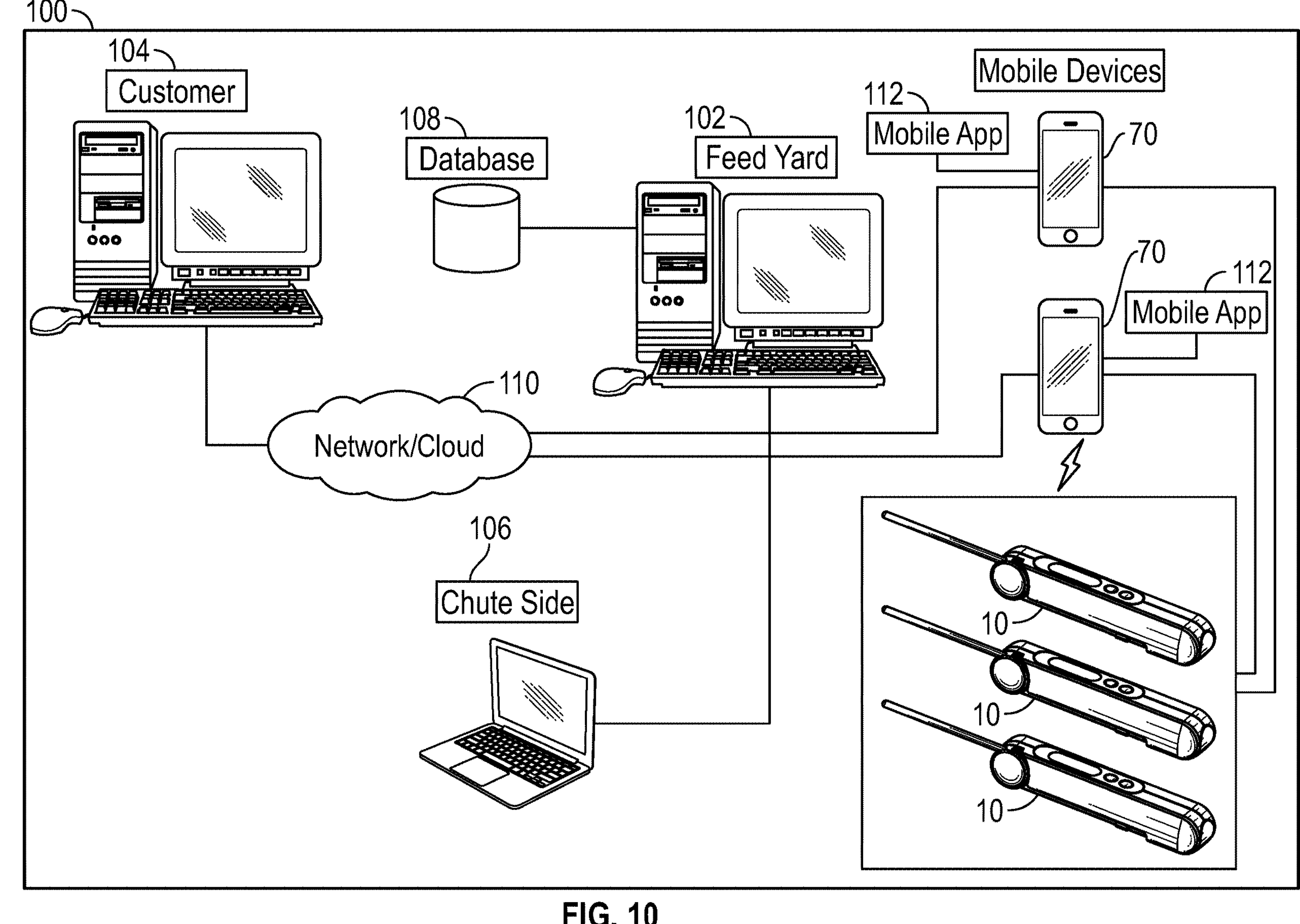
FIG. 10 is a schematic block diagram illustrating how the multifunction thermometer device may optionally be incorporated within a data communication and processing system.

FIG. 10 provides an optional and exemplary computer processing and communication network that may be used in connection with the invention. More specifically, FIG. 10 illustrates a block diagram of a system 100 that includes one or more user computers shown as feed yard computer 102, a chute side computer 106, and customer computer 104, in which each of the computers 102, 104 and 106 may alternatively comprise more than one computer.

FIG. 10 also schematically illustrates a plurality of the multifunction thermometer devices 10 for recording animal body temperature and ambient weather conditions. The devices 10 transmits wireless signals to one or more mobile communication devices 70 containing measured data including animal body temperature and ambient weather conditions, including temperature and humidity.

Each of the mobile communication devices 70 may operate to run their own mobile app 120 to process the data received from devices 10 and to generate optional treatment options for a user of the app. The processed data may further include data stored in the local database of the communication device regarding the recorded temperature and humidity, animal history, and other related data. The devices 70 communicate with the network 110 as by a web interface. The network 110 may also represent a cloud provider who facilitates communication with communication any or all communication endpoints shown in the system 10. The mobile devices 70 may communicate with any other of the computers in the system through the network 110, such as the feed yard computer system 102.

The mobile devices have their own internal computer processing capabilities with integral computer processors and other supporting hardware and software. The mobile devices may be specially configured to run the mobile software applications in order to view user interfaces and to view and update system data. All of the functionality associated with the system as applied to the computers 102, 104, and 106 may be incorporated in the mobile devices 70 as modified by mobile software applications especially adapted for the mobile device hardware and operating systems. In connection with operating systems, it should therefore be understood that the mobile devices 70 are not limited to any particular operating system, Apple iOS and Android-based systems being but two examples.

The feed yard computer 102 represents one or more computers used in a feed yard or feedlot environment used to automatically control the accounting, feeding, and treatment of animals prior to harvesting. The chute side computer 106 represents one or more computers used in a feed lot environment that may be used to initially receive and record data regarding animals being received into the feedlot. The customer computer 104 represents one or more computers of third parties who may seek to exchange data with the feed lot, such as financial institutions, cattle growers, and other third parties who are involved with a livestock industry. These user computers 102, 104, and 106 may comprise general purpose personal computers (including, merely by way of example, personal computers and/or laptop computers running various versions of Microsoft's Windows® and/or Apple® operating systems) and/or workstation computers running any of a variety of commercially-available LINUX®, UNIX® or LINUX®-like operating systems. These user computers 102, 104, and 106 may also have any of a variety of applications, including for example, database client and/or server applications, and web browser applications. Alternatively, the user computers 102, 104, and 106 may be any other electronic device, such as a thin-client computer, Internet-enabled mobile telephone, and/or personal digital assistant, capable of communicating via a network and/or displaying and navigating web pages or other types of electronic documents.

System 100 may further include a communications network 110. The network 110 may be any type of network familiar to those skilled in the art that can support data communications using any of a variety of commercially-available protocols, including without limitation TCP/IP, SNA, IPX, AppleTalk®, and the like. Merely by way of example, the communications network 110 may be a local area network ("LAN"), such as an Ethernet network, a Token-Ring network and/or the like; a wide-area network; a virtual network, including without limitation a virtual private network ("VPN"); the Internet; an intranet; an extranet; a public switched telephone network ("PSTN"); an infra-red network; a wireless network (e.g., a network operating under any of the IEEE 802.11 suite of protocols, the Bluetooth™ protocol known in the art, and/or any other wireless protocol); and/or any combination of these and/or other networks.

The feed yard computer 102 may alternatively represent a server computer. One type of server may include a web server used to process requests for web pages or other electronic documents from the mobile devices 70 and computers 104 and 106. The web server can be running an operating system including any of those discussed above, as well as any commercially-available server operating systems. The web server can also run a variety of server applications, including HTTP servers, FTP servers, CGI servers, database servers, Java servers, and the like. In some instances, the web server may publish operations available as one or more web services.

The system 100 may also include one or more file and/or application servers, which can, in addition to an operating system, include one or more applications accessible by a client running on one or more of the user computers mobile devices 70 and computers 102, 104, and 106. The file/application server(s) may be one or more general purpose computers capable of executing programs or scripts in response to the mobile devices 70 and user computers 102, 104, and 106. As one example, the server may execute one or more web applications. The web application may be implemented as one or more scripts or programs written in any programming language, such as Java®, C, C#™ or C++, and/or any scripting language, such as Perl, Python, or TCL, as well as combinations of any programming/scripting languages. The application server(s) may also include database servers, including without limitation those commercially available from Oracle®, Microsoft, Sybase®, IBM® and the like, which can process requests from database clients running on a user computer.

The system 100 may also include a database 108 for storing all data associated with running the apps 112 and running any other computer programs associated with user interfaces provided to a user regarding the functions relating to temperature, humidity, heat stress indicators or indexes, and treatment recommendations. The database, although shown at a feed yard location, may reside in a variety of different locations. By way of example, database 108 may reside on a storage medium local to (and/or resident in) one or more of the computers 102, 104, and 106. Alternatively, it may be remote from any or all of the computers 102, 104, and network 106, and in communication (e.g., via the network 110) with one or more of these. In a particular set of embodiments, the database 108 may reside in a storage-area network ("SAN"). Similarly, any necessary files for performing the functions attributed to the mobile devices 70 and computers 102, 104, and network 106 may be stored locally on the respective mobile device or computer and/or remotely, as appropriate. The database 108 may be a relational database, such as Oracle® database, that is adapted to store, In accordance with any of the computers 102, 104, and 106, these may be generally described as general-purpose computers with elements that cooperate to achieve multiple functions normally associated with general purpose computers. For example, the hardware elements may include one or more central processing units (CPUs) for processing data. The computers 102, 104, and 106 may further include one or more input devices (e.g., a mouse, a keyboard, etc.); and one or more output devices (e.g., a display device, a printer, etc.). The computers may also include one or more storage devices. By way of example, storage device(s) may be disk drives, optical storage devices, solid-state storage device such as a random access memory ("RAM") and/or a read-only memory ("ROM"), which can be programmable, flash-updateable and/or the like.

Each of the computers and servers described herein may include a computer-readable storage media reader; a communications peripheral (e.g., a modem, a network card (wireless or wired), an infra-red communication device, etc.); working memory, which may include RAM and ROM devices as described above. The server may also include a processing acceleration unit, which can include a DSP, a special-purpose processor and/or the like.

The computer-readable storage media reader can further be connected to a computer-readable storage medium, together (and, optionally, in combination with storage device (s)) comprehensively representing remote, local, fixed, and/or removable storage devices plus storage media for temporarily and/or more permanently containing computer-readable information. The computers and serve permit data to be exchanged with the network 110 and/or any other computer, server, or mobile device.

The computers and server also comprise various software elements and an operating system and/or other programmable code such as program code implementing a web service connector or components of a web service connector. It should be appreciated that alternate embodiments of a computer may have numerous variations from that described above. For example, customized hardware might also be used and/or particular elements might be implemented in hardware, software (including portable software, such as applets), or both. Further, connection to other computing devices such as network input/output devices may be employed.

It should also be appreciated that the methods described herein may be performed by hardware components or may be embodied in sequences of machine-executable instructions, which may be used to cause a machine, such as a general-purpose or special-purpose processor or logic circuits programmed with the instructions to perform the methods. These machine-executable instructions may be stored on one or more machine readable mediums, such as CD-ROMs or other type of optical disks, ROMs, RAMs, EPROMs, EEPROMs, magnetic or optical cards, flash memory, or other types of machine-readable mediums suitable for storing electronic instructions. Alternatively, the methods may be performed by a combination of hardware and software.

The term "software" as used herein shall be broadly interpreted to include all information processed by a computer processor, a microcontroller, or processed by related computer executed programs communicating with the software. Software therefore includes computer programs, libraries, and related non-executable data, such as online documentation or digital media. Executable code makes up definable parts of the software and is embodied in machine language instructions readable by a corresponding data processor such as a central processing unit of the computer. The software may be written in any known programming language in which a selected programming language is translated to machine language by a compile, interpreter or assembler element of the associated computer.

Considering the foregoing exemplary computer and communications network and elements described therein, In connection with one embodiment of the invention, it may also be considered a software program or software platform with computer coded instructions that enable execution of the functionality associated with the user interface of FIGS. 8 and 9. More specifically, the invention may be considered a software program or software platform that enables recording of body temperature, ambient temperature, and ambient humidity, and subsequently determines a heat stress level or index. The software program or platform may further include treatment options for a caregiver that are automatically generated based on predetermined logic associated with the heat stress level or index and comparison with recorded body temperature.

In connection with another embodiment of the invention, it may be considered a combined software and hardware system including (a) a software program or software platform with computer coded instructions that enable execution of the functionality associated with the user interfaces of FIGS. 8 and 9 along with the execution of one or more algorithms to generate the treatment options and (b) hardware elements including the plurality of multifunction thermometers that record temperature and humidity data.

In connection with yet another embodiment of the invention, it may be considered a sub-combination including one or more user interfaces generated by the software and the multifunction thermometer devices that provide inputs to a data processor of a computer that runs the software for purposes of generating the treatment options.

While the invention is described herein with respect to multiple preferred embodiments, it should be understood that the invention is not strictly limited to these embodiments and therefore, the invention in totality should be considered commensurate with the scope of the claims appended hereto.

What is claimed is:

1. A multifunction rectal thermometer device for measuring temperature of an animal comprising:

a housing to hold components of the device;

a fixed rotatable base secured to an end of said housing;

a single temperature probe connected to the housing by said rotatable base and selectively placed between a stored position and an extended operable position wherein the temperature probe is inserted within a rectum of the animal, and wherein the operable position defines a straight line or extension comprising the housing and the single temperature probe, said single temperature probe being rotatable about said fixed rotatable base;

a body temperature sensor incorporated in said temperature probe at a distal end thereof and said body temperature sensor especially adapted for measuring rectal temperature of an animal;

a display module secured to said housing for displaying measured temperature and other selected measured parameters;

control buttons on said housing to control operation of the device;

an ambient temperature sensor within said housing;

an ambient humidity sensor within said housing;

a microprocessor within said housing and communicating with each of said sensors;

a data storage element communicating with said microprocessor for storing information processed by said microprocessor including temperature data including the animal body temperature, the ambient temperature and present humidity conditions; and a wireless radio;

wherein said temperature probe further includes a sleeve and a probe extension extending distally from said sleeve;

wherein a heating coil is disposed in said temperature probe and in contact with said probe extension to thereby selectively heat said body temperature sensor prior to use; and wherein the heating coil includes wraps of wire that are located at a proximal end of the probe extension.

2. The device, as claimed in claim 1, wherein:

said probe extension is made of a heat conductive material including copper.

3. The device, as claimed in claim 1, wherein:

said rotatable base interconnects a proximal end of said temperature probe to said housing enabling said temperature probe to be placed in the stored position or the extended position.

4. The device, as claimed in claim 1, wherein:

the control buttons communicate with said microprocessor enabling a user to selectively control functions of said device.

5. The device, as claimed in claim 1, further including:

an RFID reader disposed in said housing and communicating with said microprocessor, said RFID reader receiving identification data associated with the animal from a tag of the animal, said RFID reader providing said identification data to said microprocessor and stored in said data storage element wherein the identification data and temperature are linked for each animal whose temperature is taken.

6. The device of claim 1, further wherein:

a calculated temperature heat index (THI) is displayed on said display module, wherein the temperature heat index is a measure of the degree to which the ambient temperature and the humidity places stress on an animal, which automatically triggers a display of a recommended treatment for the animal.

7. The device of claim 1, wherein:

the distal end of the temperature probe has a bulbous shaped tip.

8. A multifunction rectal thermometer device for measuring temperature of an animal comprising:

a housing to hold components of the device;

a rotatable base secured to an end of said housing;

a single temperature probe connected to the housing by said rotatable base and selectively placed between a stored position and an extended operable position wherein the temperature probe is inserted within a rectum of the animal, and wherein the operable position defines a straight line or extension comprising the housing and the single temperature probe;

a body temperature sensor incorporated in said temperature probe at a distal end thereof and said body temperature sensor especially adapted for measuring rectal temperature of an animal;

a display module secured to said housing for displaying measured temperature and other selected measured parameters;

control buttons on said housing to control operation of the device;

an ambient temperature sensor within said housing;

an ambient humidity sensor within said housing;

a microprocessor within said housing and communicating with each of said sensors; and a data storage element communicating with said microprocessor for storing information processed by said microprocessor including temperature data including the animal body temperature, the ambient temperature, and present humidity conditions;

wherein a heat stress indication is automatically determined by said processor, the heat stress indication being a logical relationship established between the animal body temperature and the ambient temperature and humidity conditions; and wherein a calculated temperature heat index (THI) is displayed on said display module, wherein the temperature heat index is a measure of the degree to which the ambient temperature and the humidity places stress on the animal, which automatically triggers a display of a recommended treatment for the animal.

9. The multifunction rectal thermometer device of claim 8, wherein:

the device includes a system that comprises at least one user interface on a remote communication device that communicates with said multifunction rectal thermometer device, the at least one user interface including a representation of said heat stress indication.

10. The multifunctional rectal thermometer device of claim 8, wherein:

the distal end of the temperature probe has a bulbous shaped tip.

* * * * *